US009439885B2

(12) United States Patent
Petschow

(10) Patent No.: US 9,439,885 B2
(45) Date of Patent: Sep. 13, 2016

(54) METHOD FOR INHIBITING THE GROWTH OF BACTERIA

(75) Inventor: Bryon W. Petschow, Ewing, NJ (US)

(73) Assignee: Mead Johnson Nutrition Company, Glenview, IL (US)

( * ) Notice: Subject to any disclaimer, the term of this patent is extended or adjusted under 35 U.S.C. 154(b) by 740 days.

(21) Appl. No.: 12/429,571

(22) Filed: Apr. 24, 2009

(65) Prior Publication Data
US 2009/0298937 A1    Dec. 3, 2009

Related U.S. Application Data

(60) Provisional application No. 61/058,243, filed on Jun. 3, 2008.

(51) Int. Cl.
| *A61K 31/225* | (2006.01) |
| *A61K 31/23* | (2006.01) |
| *A23L 1/29* | (2006.01) |
| *A23L 1/30* | (2006.01) |

(52) U.S. Cl.
CPC ............ *A61K 31/23* (2013.01); *A23L 1/296* (2013.01); *A23L 1/3008* (2013.01); *A23L 1/3014* (2013.01); *A23V 2002/00* (2013.01)

(58) Field of Classification Search
CPC ..... A61K 31/23; A23L 1/3014; A23L 1/296; A23L 1/3008; A23V 2002/00
USPC ........................................................ 514/547
See application file for complete search history.

(56) References Cited

U.S. PATENT DOCUMENTS

| 4,298,624 A | 11/1981 | Mehring et al. |
| 4,670,285 A | 6/1987 | Clandinin et al. |
| 4,931,300 A | 6/1990 | Monte |
| 5,270,188 A | 12/1993 | Yamaguchi et al. |
| 5,624,958 A | 4/1997 | Isaacs et al. |
| 5,780,039 A | 7/1998 | Greenberg et al. |
| 5,866,606 A * | 2/1999 | Schaller et al. ............. 514/547 |
| 5,908,862 A | 6/1999 | Wai Lee et al. |
| 5,958,974 A | 9/1999 | Anderson et al. |
| 5,981,587 A * | 11/1999 | Guzman-Harty et al. .... 514/546 |
| 6,033,705 A | 3/2000 | Isaacs |
| 6,077,558 A | 6/2000 | Euber |
| 6,228,886 B1 | 5/2001 | Anderson et al. |
| 6,428,832 B2 | 8/2002 | Van Den Burg et al. |
| 6,436,464 B1 | 8/2002 | Euber |
| 6,638,978 B1 | 10/2003 | Kabara |
| 6,699,907 B1 | 3/2004 | Dee et al. |
| 6,824,801 B2 | 11/2004 | Yajima et al. |
| 6,838,431 B2 | 1/2005 | Portman |
| 7,090,879 B2 | 8/2006 | Albrecht et al. |
| 2003/0152664 A1 | 8/2003 | Couzy et al. |
| 2004/0101596 A1 | 5/2004 | Ndife et al. |
| 2006/0189535 A1* | 8/2006 | Kaudsen ...................... 514/12 |
| 2007/0009495 A1* | 1/2007 | McMahon et al. ......... 424/93.7 |
| 2007/0104700 A1* | 5/2007 | Garcia-Rodenas et al. .. 514/547 |
| 2007/0254062 A1 | 11/2007 | Sighal et al. |
| 2008/0032002 A1* | 2/2008 | Anthony et al. ............... 426/72 |
| 2009/0246337 A1* | 10/2009 | Braun et al. .............. 426/330.3 |

FOREIGN PATENT DOCUMENTS

| EP | 1688049 | 8/2006 |
| JP | 401080250 A | 3/1989 |
| JP | 3094660 A | 4/1991 |
| JP | 404197146 A | 7/1992 |

OTHER PUBLICATIONS

"Fatty Acids and Derivatives as Antimicrobial Agents," Jon J. Kabara, Dennis M. Swieczkowski, Anthony J. Conley, and Jospeh P. Truant, Antimicrobial Agents and Chemotherapy, Jul. 1972, p. 23-28, vol. 2, No. 1.
Impact of medium-chain monoglycerides on intestinal colonisatin by Vigrio cholerae or enterotoxigenic *Escherichia coli*, Bryon W. Petschow, Rosanne P. Batema, Roert D. Talbott and Lorna L. Ford, 1998 The Pathological Society of Great Britain and Ireland.
"A Review of Monolaurin and Lauric Acid—Natural Virucidal and Bactericidal Agents" Shari Lieberman, Ph.D., C.N.S., F.A.C.N., Mary G. Enig, Ph.D., C.N.S., M.A.C.N., and Harry G. Preuss, M.D., C.N.S., M.A.C.N., Alternative & Complementary Therapies—Dec. 2006.
"Filtration Knocks Out Deadly Bacteria in Nursery," Anita Garem, Food Quality, Apr./May 2005.
"Mother's Milk the First Nutriceutical," http://www.lauricidin.com/mothers_milk.htm, Mar. 29, 2007, copyright 2005 Med-Chem Labs Inc.
"Lipid Coated Viruses (LCVs) and Bacteria (LCBs)," http://www.lauric.org/lcv.html, Mar. 29, 2007, copyright 2001 lauric.org.
"Laurcidin vs. Coconut Oil," http://www.lauricidin.com/lauricidin.coconut.htm, Mar. 12, 2007, copyright 2005 Med-Chem Labs Inc.

* cited by examiner

*Primary Examiner* — Jason Sims
*Assistant Examiner* — Ibrahim D Bori
(74) *Attorney, Agent, or Firm* — Patterson Intellectual Property Law, P.C.; James R. Cartiglia; Hilary Dorr Lang

(57) ABSTRACT

The present invention is directed to a method for inhibiting the growth of pathogenic bacteria in an infant formula comprising supplementing the infant formula with at least one diglyceride antimicrobial agent.

17 Claims, No Drawings

METHOD FOR INHIBITING THE GROWTH OF BACTERIA

BACKGROUND OF THE INVENTION

Field of the Invention

The present invention relates generally to a method for inhibiting the growth of pathogenic bacteria in an infant formula.

SUMMARY OF THE INVENTION

Briefly, therefore, the present invention is directed to a novel method for inhibiting the growth of pathogenic bacteria in an infant formula comprising supplementing the infant formula with at least one diglyceride antimicrobial agent.

In another aspect, the present invention is a method for inhibiting the growth of *Enterobacter sakazakii* (*E. sakazakii*) in an infant formula comprising supplementing the infant formula with at least one diglyceride.

In yet another aspect, the present invention is a method for inhibiting the growth of *H. pylori* in an infant formula comprising supplementing the infant formula with at least one diglyceride.

DETAILED DESCRIPTION OF THE PREFERRED EMBODIMENTS

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment.

Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

The term "infant" means a human that is less than about 18 months of age.

The term "child" means a human that is between about 18 months and 12 years of age. In some embodiments, a child is between the ages of about 18 months and 6 years. In other embodiments, a child is between the ages of about 7 and 12 years.

As used herein, the term "infant formula" means a composition that satisfies the nutrient requirements of an infant by being a substitute for human milk.

Diglycerides, also referred to as diacylglycerols, are glycerides consisting of two fatty acid chains covalently bonded to a glycerol molecule through ester linkages. Diglycerides can have many different combinations of fatty acids attached at the C-1 and C-2 positions.

Diglycerides are natural components of various edible oils that are found in low amounts in all vegetable oils. They are used in small quantities in some foods as emulsifiers, and are often found in bakery products, beverages, ice cream, chewing gum, shortening, whipped toppings, mayonnaise, margarine, and confections. In recent years, diglycerides have received interest from researchers in food science, biochemistry, and nutrition because of the wide spectrum of benefits provided by diglycerides, including delaying the progression of renal failure and promoting weight loss.

Diglycerides are important intermediates in the biosynthesis of triglycerides and phospholipids, and play a fundamental role in cellular signaling. They act as signaling molecules by binding directly to many different proteins and further regulate cell growth and apoptosis. Diglycerides can activate cellular mechanisms directly via protein activation or indirectly via the liberation of fatty acids, which may be metabolized in agonist molecules.

The structure of diglyceride is shown below:

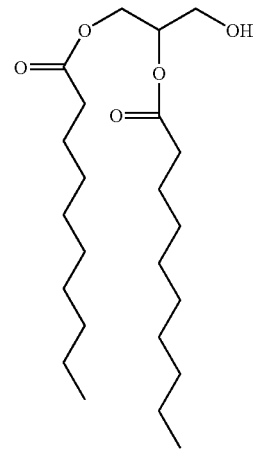 [SMILES: CCCCCCCCCC(=O)OCC(CO)OC(=O)CCCCCCCCC]

As noted, the present invention is directed to a method for inhibiting the growth of pathogenic bacteria in an infant formula comprising supplementing the infant formula with at least one diglyceride antimicrobial agent. The pathogenic bacterial growth inhibited through the method of the invention may, in an embodiment, be any pathogenic bacteria known in the art, including any member of the group Enterobacteriaceae. In another embodiment, the pathogenic bacteria which experience growth inhibition as a result of the invention may be *Vibrio cholerae, Escherichia coli, Shigella sonnei, Salmonella typhi, E. sakazakii,* or *Helicobacter pylori* (*H. pylori*). In a particular embodiment, the pathogenic bacterium is *E. sakazakii*. In another embodiment, the pathogenic bacterium inhibited by the method of the present invention is *H. pylori*.

In an embodiment of the invention, the infant formula contains an amount of diglyceride that is between about 0.25 and 10 g per L of formula. In another embodiment of the invention, the infant formula contains an amount of diglyceride that is between about 2.5 and 5 g per L of formula. In a particular embodiment of the invention, the infant formula contains an amount of diglyceride that is about 2.5 g per L of formula.

As used in the present invention, the source of diglyceride can be any source known in the art such as plant material, animal material, synthetic material, and the like. Commercial sources of diglyceride may be either animal (typically, cow- or hog-derived) or vegetable (derived primarily from soy bean and canola oil).

In an embodiment of the invention, the diglyceride inhibits the growth of either or both of gram-positive and gram-negative bacteria.

In another embodiment, the diglyceride may be effective in inhibiting bacterial growth in nutritional compositions, children's nutritional products, or human milk fortifiers or supplements. Thus, the method of the invention may be useful for inhibiting the growth of pathogenic bacteria in products for a human infant, child, or adult.

The infant formula of the invention can be a term infant formula or a preterm infant formula. The infant formula of the invention can further be a liquid (ready-to-use or concentrated) or powder. If the infant formula of the invention is a powder, it may be reconstituted to liquid form with water prior to use.

In the invention, an infant formula is supplemented with at least one diglyceride. In a particular embodiment, the infant formula is supplemented with at least two diglycerides. In another embodiment, the infant formula is supplemented with at least three diglycerides.

In an embodiment, the infant formula of the invention may be nutritionally complete and contain suitable types and amounts of lipids, carbohydrates, proteins, vitamins and minerals. The amount of lipid or fat typically can vary from about 3 to about 7 g per 100 kcal. The amount of protein typically can vary from about 1 to about 5 g per 100 kcal. The amount of carbohydrate typically can vary from about 8 to about 12 g per 100 kcal. Protein sources can be any used in the art, e.g., nonfat milk, whey protein, casein, soy protein, hydrolyzed protein, amino acids, and the like. Carbohydrate sources can be any used in the art, e.g., lactose, glucose, corn syrup solids, maltodextrins, sucrose, starch, rice syrup solids, and the like. Lipid sources can be any used in the art, e.g., vegetable oils such as palm oil, canola oil, corn oil, soybean oil, palmolein, coconut oil, medium chain triglyceride oil, high oleic sunflower oil, high oleic safflower oil, and the like.

Conveniently, commercially available infant formula can be used. For example, Enfamil®, Enfamil® Premature Formula, Enfamil® with Iron, Enfamil® LIPIL®, Lactofree®, Nutramigen®, Pregestimil®, and ProSobee® infant formulas (available from Mead Johnson & Company, Evansville, Ind., U.S.A.) may be supplemented with suitable levels of diglyceride and used in practice of the method of the invention.

In some embodiments of the invention, the infant formula may be supplemented with at least one other antimicrobial agent. This other antimicrobial agent may be any antimicrobial agent known in the art, assuming it is compatible with the other components of the infant formula. These other antimicrobial agents may be fatty alcohols, monoglycerides, and/or free fatty acids and their corresponding esters, including monoglycerol esters.

In some embodiments of the invention, the infant formula containing at least one diglyceride may be supplemented with additional components. These additional components may include probiotics, prebiotics, or long chain polyunsaturated fatty acids (LCPUFAs).

The term "probiotic" means a microorganism that exerts beneficial effects on the health of the host. Any probiotic known in the art may be used, provided it is suitable for supplementing an infant formula containing diglyceride. For example, the probiotic may be chosen from the group consisting of *Lactobacillus* and *Bifidobacterium*. Alternatively, the probiotic can be *Lactobacillus rhamnosus* GG.

The term "prebiotic", as used herein, means a non-digestible food ingredient that stimulates the growth and/or activity of probiotics. In this embodiment, any prebiotic known in the art may be used, provided it is suitable for supplementing an infant formula containing diglyceride. In a particular embodiment, the prebiotic can be selected from the group consisting of fructo-oligosaccharide, gluco-oligosaccharide, galacto-oligosaccharide, inulin, isomalto-oligosaccharide, polydextrose, xylo-oligosaccharide, lactulose, and combinations thereof.

While not wishing to be bound to this or any theory, it is believed that a method for inhibiting the growth of pathogenic bacteria in an infant formula supplemented with prebiotics and diglycerides may provide a synergistic effect. More specifically, it is believed that the prebiotic may alter the composition of the gut flora to provide a greater number of beneficial bacteria and fewer pathogenic bacteria, further contributing to the antimicrobial effect of the diglyceride in the present invention.

Furthermore, it is believed that a method for inhibiting the growth of pathogenic bacteria in an infant formula supplemented with probiotics and diglycerides may provide a synergistic effect. More specifically, it is believed that the probiotic may alter the composition of the gut flora to provide a greater number of beneficial bacteria and fewer pathogenic bacteria, further contributing to the antimicrobial effect of the diglyceride in the present invention.

In yet another embodiment of the invention, the infant formula may be supplemented with LCPUFAs and at least one diglyceride. In this embodiment, the LCPUFAs may include docosahexaenoic acid (DHA), arachidonic acid (ARA), and/or eicosapentaenoic acid (EPA).

If the infant formula is supplemented with LCPUFAs as part of the present invention, the weight ratio of ARA:DHA may be from about 1:3 to about 9:1. In one embodiment of the present invention, this ratio is from about 1:2 to about 4:1. In yet another embodiment, the ratio is from about 2:3 to about 2:1. In one particular embodiment the ratio is about 2:1. In another particular embodiment of the invention, the ratio is about 1:1.5. In other embodiments, the ratio is about 1:1.3. In still other embodiments, the ratio is about 1:1.9. In a particular embodiment, the ratio is about 1.5:1. In a further embodiment, the ratio is about 1.47:1.

If the infant formula is supplemented with DHA as part of the present invention, the level of DHA may be between about 0.0% and 1.00% of fatty acids, by weight. In other embodiments, the level of DHA may be about 0.32% by weight. In some embodiments, the level of DHA may be about 0.33% by weight. In another embodiment, the level of DHA may be about 0.64% by weight. In another embodiment, the level of DHA may be about 0.67% by weight. In yet another embodiment, the level of DHA may be about 0.96% by weight. In a further embodiment, the level of DHA may be about 1.00% by weight.

If the infant formula is supplemented with ARA as part of the present invention, the level of ARA may be between 0.0% and 0.67% of fatty acids, by weight. In another embodiment, the level of ARA may be about 0.67% by weight. In another embodiment, the level of ARA may be about 0.5% by weight. In yet another embodiment, the level of DHA may be between about 0.47% and 0.48% by weight.

If the infant formula is supplemented with DHA as part of the present invention, the amount of DHA may be from about 2 mg per 100 kilocalories (kcal) to about 100 mg per 100 kcal. In another embodiment, the amount of DHA may be from about 5 mg per 100 kcal to about 75 mg per 100 kcal. In yet another embodiment, the amount of DHA may be from about 15 mg per 100 kcal to about 60 mg per 100 kcal.

If the infant formula is supplemented with ARA as part of the present invention, the amount of ARA may be from about 4 mg per 100 kilocalories (kcal) to about 100 mg per 100 kcal. In another embodiment, the amount of ARA may be from about 10 mg per 100 kcal to about 67 mg per 100 kcal. In yet another embodiment, the amount of ARA may be from about 20 mg per 100 kcal to about 50 mg per 100 kcal. In a particular embodiment, the amount of ARA may be from about 25 mg per 100 kcal to about 40 mg per 100 kcal. In one embodiment, the amount of ARA is about 30 mg per 100 kcal.

If the infant formula is supplemented with DHA as part of the present invention, the effective amount of DHA may be from about 3 mg per kg of body weight per day to about 150 mg per kg of body weight per day. In one embodiment of the invention, the amount is from about 6 mg per kg of body weight per day to about 100 mg per kg of body weight per day. In another embodiment the amount is from about 15 mg per kg of body weight per day to about 60 mg per kg of body weight per day.

If the infant formula is supplemented with ARA as part of the present invention, the effective amount of ARA may be from about 5 mg per kg of body weight per day to about 150 mg per kg of body weight per day. In one embodiment of this invention, the amount varies from about 10 mg per kg of body weight per day to about 120 mg per kg of body weight per day. In another embodiment, the amount varies from about 15 mg per kg of body weight per day to about 90 mg per kg of body weight per day. In yet another embodiment, the amount varies from about 20 mg per kg of body weight per day to about 60 mg per kg of body weight per day.

If the infant formula of the invention is supplemented with oils containing LCPUFAs, it may be accomplished using standard techniques known in the art. For example, an equivalent amount of an oil which is normally present in a composition, such as high oleic sunflower oil, may be replaced with the LCPUFAs.

If utilized, the source of the LCPUFAs can be any source known in the art such as marine oil, fish oil, single cell oil, egg yolk lipid, brain lipid, and the like. The LCPUFAs can be in natural form or refined form.

In an embodiment, the invention comprises a method of inhibiting the growth of pathogenic bacteria in a nutritional composition, the method comprising adding at least one diglyceride to the nutritional composition. In a particular embodiment, the invention comprises a method of inhibiting the growth of *E. sakazakii* in a powdered infant formula, the method comprising adding at least one diglyceride to the infant formula. In yet another embodiment, the invention comprises a method of inhibiting the growth of *H. pylori* in a powdered infant formula, the method comprising adding at least one diglyceride to the infant formula.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and is not intended to limit the invention so further described in such appended claims. Therefore, the spirit and scope of the appended claims should not be limited to the description of the preferred versions contained therein.

What is claimed is:

1. A method for inhibiting the growth of pathogenic bacteria in an infant formula, the method comprising the steps of supplementing the infant formula with between about 6 g and about 10 g of at least one diglyceride antimicrobial agent per liter of infant formula and further supplementing the infant formula with a monoglyceride, wherein the diglyceride antimicrobial agent consists of two fatty acid chains covalently bound to a glycerol molecule through ester linkages.

2. The method of claim 1 additionally comprising supplementing the infant formula with at least one long chain polyunsaturated fatty acid.

3. The method of claim 2 wherein the long chain polyunsaturated fatty acid is selected from the group consisting of docosahexaenoic acid, arachidonic acid, eicosapentaenoic acid and combinations thereof.

4. The method of claim 1 additionally comprising supplementing the infant formula with at least one probiotic selected from the group consisting of *Lactobacillus* and Bifidobacteria.

5. The method of claim 1 additionally comprising supplementing the infant formula with at least one prebiotic.

6. The method of claim 1 wherein the infant formula is further supplemented with at least one additional antimicrobial agent.

7. The method of claim 6 wherein the at least one additional antimicrobial agent is selected from the group consisting of a fatty alcohol, a monoglyceride, a free fatty acid, the corresponding ester of a free fatty acid, and combinations thereof.

8. The method of claim 1 wherein the pathogenic bacteria inhibited by the diglyceride is selected from the group consisting of gram-positive bacteria, gram-negative bacteria, and combinations thereof.

9. The method of claim 1 wherein the infant formula is a powdered formula.

10. The method of claim 1 wherein the infant formula is in liquid form.

11. The method of claim 1 wherein the pathogenic bacteria comprises *E. sakazakii*.

12. A method for inhibiting the growth of *Helicobacter pylori* in an infant formula, the method comprising the steps of supplementing the infant formula with between about 6 g and about 10 g of at least one diglyceride antimicrobial agent per liter of infant formula and further supplementing the infant formula with a monoglyceride, wherein the diglyceride antimicrobial agent consists of two fatty acid chains covalently bound to a glycerol molecule through ester linkages.

13. The method of claim 12 further comprising the step of supplementing the infant formula with a probiotic chosen from the group consisting of *Lactobacillus* and Bifidobacteria.

14. The method of claim 13, wherein the probiotic is *Lactobacillus rhamnosus* GG.

15. The method of claim 12 further comprising the step of supplementing the infant formula with at least one other antimicrobial agent selected from the group selected from the group consisting of a fatty alcohol, a monoglyceride, a free fatty acid, the corresponding ester of a free fatty acid, and combinations thereof.

16. A method for inhibiting the growth of pathogenic bacteria selected from the group consisting of *Vibrio cholerae, Escherichia coli, Shigella sonnei, Salmonella typhi, E. sakazakii*, and *Helicobacter pylori* in an infant formula, the method comprising the steps of supplementing the infant formula with between about 6 g and about 10 g of at least two diglycerides per liter of infant formula and further supplementing the infant formula with a monoglyceride, wherein the diglycerides consist of two fatty acid chains covalently bound to a glycerol molecule through ester linkages.

17. The method of claim 16, wherein the infant formula is supplemented with between about 6 g and about 10 g of at least three diglycerides per liter of infant formula.

* * * * *